(12) United States Patent
Tamiev et al.

(10) Patent No.: US 12,344,873 B2
(45) Date of Patent: Jul. 1, 2025

(54) ANAEROBIC PRECONDITIONING OF CELLS FOR IMPROVED IN VITRO PROTEIN PRODUCTION

(71) Applicant: Iowa State University Research Foundation, Inc., Ames, IA (US)

(72) Inventors: Denis Tamiev, Ames, IA (US); Nigel Forest Reuel, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 468 days.

(21) Appl. No.: 17/689,586

(22) Filed: Mar. 8, 2022

(65) Prior Publication Data

US 2022/0282286 A1   Sep. 8, 2022

Related U.S. Application Data

(60) Provisional application No. 63/158,044, filed on Mar. 8, 2021.

(51) Int. Cl.
| | |
|---|---|
| C12P 1/04 | (2006.01) |
| C12N 1/20 | (2006.01) |
| C12P 21/00 | (2006.01) |
| C12R 1/19 | (2006.01) |

(52) U.S. Cl.
CPC ............... *C12P 1/04* (2013.01); *C12N 1/205* (2021.05); *C12P 21/00* (2013.01); *C12N 2500/02* (2013.01); *C12N 2500/05* (2013.01); *C12N 2500/34* (2013.01); *C12N 2500/46* (2013.01); *C12R 2001/19* (2021.05)

(58) Field of Classification Search
None
See application file for complete search history.

(56) References Cited

U.S. PATENT DOCUMENTS

2018/0016614 A1*  1/2018  Jewett .................. C12N 9/1247
2021/0171584 A1*  6/2021  Jewett ...................... C12N 1/20

OTHER PUBLICATIONS

Echavarri-Erasun et al. (Methods Mol Biol. 2014:1122:19-31 (Year: 2014).*
Asakura, T., et al., "Stabilizing Effect of Various Organic Solvents on Protein", J. Biol. Chem., 253(18), (1978), 6423-6425.
Cole, J. A., et al., "Nitrite Reduction to Ammonia by Fermentative Bacteria: A Short Circuit in the Biological Nitrogen Cycle", FEMS Microbiol. Lett., 7(2), (1980), 65-72.
Cole, J. A., et al., "The Rapid Accumulation of Large Quantities of Ammonia during Nitrite Reduction by *Escherichia coli*", FEMS Microbiol. Lett., 4(6), (1978), 327-329.
Cole, S. D., et al., "Methodologies for Preparation of Prokaryotic Extracts for Cell-Free Expression Systems", Synth. Syst. Biotechnol., 5(4), (2020), 252-267.
Contreras-Llano, L. E., et al., "Holistic Engineering of Cell-Free Systems through Proteome-Reprogramming Synthetic Circuits", Nat. Commun., 11(1), 3138, (2020), 1-10.
Dopp, J. L., et al., "Methods to Reduce Variability in *E. coli*-Based Cell-Free Protein Expression Experiments", Synth. Syst. Biotechnol., 4(4), (2019), 204-211.
Dopp, J. L., et al., "Process Optimization for Scalable *E. coli* Extract Preparation for Cell-Free Protein Synthesis", Biochem. Eng. J., 138, (2018), 21-28.
Gregorio, N. E., et al., "A User's Guide to Cell-Free Protein Synthesis", Methods Protoc., 2(1): 24, (2019), 34 pgs.
Jewett, M. C., et al., "An Integrated Cell-Free Metabolic Platform for Protein Production and Synthetic Biology", Mol. Syst. Biol., 4: 220, (2008), 1-10.
Kato, A., et al., "Cell-Sized Confinement in Microspheres Accelerates the Reaction of Gene Expression", Sci. Rep., 2: 283, (2012), 1-5.
Kelwick, R., et al., "Development of a *Bacillus subtilis* Cell-Free Transcription-Translation System for Prototyping Regulatory Elements", Metab. Eng., 38, (2016), 370-381.
Kwon, Y.-C., et al., "High-Throughput Preparation Methods of Crude Extract for Robust Cell-Free Protein Synthesis", Sci. Rep., 5(1), 8663, (2015).
Lin, X., et al., "$O_2$-Tuned Protein Synthesis Machinery in *Escherichia coli*-Based Cell-Free System", Front. Bioeng. Biotechnol., 8: 312, (2020), 1-11.
Pardee, K., et al., "Portable, On-Demand Biomolecular Manufacturing", Cell, 167(1), (2016), 248-259.
Pedersen, A., et al., "Rational Improvement of Cell-Free Protein Synthesis", New Biotechnol., 28(3), (2011), 218-224.
Richter, K., et al., "Dissimilatory Reduction of Extracellular Electron Acceptors in Anaerobic Respiration", Appl. Environ. Microbiol., 78 (4), (2012), 913-921.
Salehi, Amin S., et al., "Cell-Free Protein Synthesis of a Cytotoxic Cancer Therapeutic: Onconase Production and a Just-Add-Water Cell-Free System.", Biotechnology Journal, 11(2), (2016), 274-281.
Silverman, A. D., et al., "Deconstructing Cell-Free Extract Preparation for in Vitro Activation of Transcriptional Genetic Circuitry", ACS Synth. Biol., 8(2), (2019), 403-414.
Simon, J., et al., "Diversity and Evolution of Bioenergetic Systems Involved in Microbial Nitrogen Compound Transformations", Biochim. Biophys. Acta BBA—Bioenerg., 1827(2), (2013), 114-135.
Tao, H., et al., "Functional Genomics: Expression Analysis of *Escherichia coli* Growing on Minimal and Rich Media", J. Bacteriol., 181(20), (1999), 6425-6440.
Voloshin, A. M., et al., "Efficient and Scalable Method for Scaling up Cell Free Protein Synthesis in Batch Mode", Biotechnol. Bioeng., 91(4), (2005), 516-521.

(Continued)

*Primary Examiner* — Christian L Fronda
(74) *Attorney, Agent, or Firm* — Schwegman Lundberg & Woessner, P.A.

(57) ABSTRACT

Various aspects relate to a cell-free protein expression method. The method includes exposing a microorganism to substantially anaerobic growth conditions to produce a conditioned microorganism. The method further includes lysing the conditioned microorganism to produce a lysate. The method further includes combining the lysate with a nucleic acid and producing a protein of interest a metabolic pathway, a molecule, or a mixture thereof from the lysate.

14 Claims, 6 Drawing Sheets

(56) References Cited

OTHER PUBLICATIONS

Wang, H., et al., "The NrfA and NirB Nitrite Reductase Operons in *Escherichia coli* Are Expressed Differently in Response to Nitrate than to Nitrite", J. Bacteriol., 182(20), (2000), 5813-5822.

Wang, X, et al., "The Role of the NADH-Dependent Nitrite Reductase, Nir, from *Escherichia coli* in Fermentative Ammonification.", Arch. Microbiol., 201(4), (2019), 519-530.

Zawada, J. F., et al., "Microscale to Manufacturing Scale-up of Cell-Free Cytokine Production—a New Approach for Shortening Protein Production Development Timelines", Biotechnol. Bioeng., 108(7), (2011), 1570-1578.

Zimmerman, E. S., et al., "Production of Site-Specific Antibody-Drug Conjugates Using Optimized Non-Natural Amino Acids in a Cell-Free Expression System", Bioconjug. Chem., 25(2), (2014), 351-361.

\* cited by examiner

ANAEROBIC PRECONDITIONING OF CELLS FOR IMPROVED IN VITRO PROTEIN PRODUCTION

RELATED APPLICATION

This application claims priority to U.S. Provisional Patent Application No. 63/158,044, titled "ANAEROBIC PRECONDITIONING OF CELLS FOR IMPROVED IN VITRO PROTEIN PRODUCTION" and filed on Mar. 8, 2021, the contents of which are hereby incorporated by reference.

STATEMENT OF GOVERNMENT SUPPORT

This invention was made with government support under R35 GM138265 awarded by the National Institutes of Health. The government has certain rights in the invention.

BACKGROUND

Production of proteins or other molecules of interest can be accomplished using cell-free protein synthesis. However, initial production and ultimate titer of the proteins or other molecules produced can be low. There is a need in the art to improve cell-free protein synthesis techniques.

SUMMARY OF THE DISCLOSURE

Various aspects relate to a cell-free protein expression method. The method includes exposing a microorganism to substantially anaerobic growth conditions to produce a conditioned microorganism. The method further includes lysing the conditioned microorganism to produce a lysate. The method further includes combining the lysate with a nucleic acid and producing a protein of interest, a metabolic pathway, a molecule, or a mixture thereof from the lysate.

BRIEF DESCRIPTION OF THE FIGURES

The drawings illustrate generally, by way of example, but not by way of limitation, various embodiments discussed in the present document.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

According to various aspects, the instant disclosure relates to a cell-free protein expression method. In vitro protein expression is the production of recombinant proteins in solution using biomolecular translation machinery extracted from cells. Because protein synthesis occurs in cell lysates rather than within cultured cells, the method is also called cell-free protein expression. Cell-free protein production can be accomplished with several kinds and species of cell extract, and these approaches have several advantages and features that complement traditional in vivo methods.

Cell-free protein expression can be useful in many different potential applications. Examples of such applications can include experiments to characterize protein-protein interactions and protein-nucleic acid interactions. Another example can include rapid and high-throughput expression of mutant or truncated proteins for functional analysis. Another example can include expression of mammalian proteins with proper glycosylation and native post-translational modifications (PTMs), another example can include labeling of proteins with stable isotopes for structural analysis. Another example can include production of functional virons or toxic polypeptides. Another example can include analysis of components required for protein folding, protein stability or protein degradation. Other examples of uses not specifically recited here are also within the scope of this disclosure. Cell-free Protein Synthesis (CFPS) removes time consuming constraints of working with live cells and allows for rapid prototyping of proteins and genetic elements. It is also being used for commercial production of specialized, cytotoxic biologics and is a proposed method of distributed, on-demand biomanufacturing to respond to local outbreaks. CFPS reactions include of a combination of cell lysate, metabolic supplements, and DNA template. The quantities of each are optimized to increase the amount of active or correctly folded protein product. While a large body of literature describes cell strain modifications and general process improvements to optimize the yield of CFPS reactions, the preconditioning of cells to maximize production of adenosine triphosphate (ATP) in the absence of oxygen has never been reported. Although, anaerobic cell lysis has been used to prepare extract suitable for oxygen sensitive expression targets such as hydrogenases, and, very recently, improved oxygen transport in CFPS reactions has shown to improve productivity, optimization of lysate during the growth phase through preconditioning cells for anaerobic metabolism has never been attempted.

One of the main roles of oxygen is to serve as a terminal electron acceptor (TEA) which allows for efficient generation of ATP via oxidative phosphorylation. ATP, the energy currency of the cell, is used in countless enzymatic reactions and thus is a limited resource that, in part, determines the productivity and longevity of CFPS reactions. Oxygen accessibility has been shown to be a limiting condition for CFPS reactions. Conventional methods of increasing accessibility to oxygen such as vigorous shaking or sparging with gas are not as useful in CFPS reactions as they cause significant protein unfolding. It was also previously demonstrated that increasing the surface area to volume ratio of CFPS reaction vessels can be beneficial. However, this approach has its limitations for two reasons—(1) it increases the rate of evaporation, and (2) it is problematic when working with manufacturing scale volumes. An alternative strategy to maximizing the efficiency of CFPS would be to remove the dependence on oxygen by preconditioning the cells used for lysate to work with an alternative TEA.

*E. coli* is a facultative aerobe that can use a variety of TEA when oxygen is not available or limited. In addition, *E. coli* can temporarily survive without any TEA by producing ethanol, lactate or acetate. This process is called anaerobic fermentation "AF"). AF is defined as the metabolic pathway that starts with glucose which is then converted to either lactate or ethanol as a result of several enzymatic steps that conclude with alcohol or lactate dehydrogenases. It is understood that AF exists to regenerate $NAD^+$ while the electron transport chain (ETC) is inactive due to the inaccessibility of TEAs. This mechanism is temporary, as cellular growth is inhibited when the concentration of alcohol or acid in the media surpasses a certain threshold.

*E. coli* has evolved to use alternative electron acceptors to maintain the activity of the ETC when oxygen is not available. Nar pathway of nitrogen metabolism which uses nitrate as an intermediate electron acceptor and nitrite as terminal acceptor is examined. However, it is important to note that this is not the only anaerobic nitrogen metabolism pathway, and, *E. coli*, among many other bacteria can use a variety of TEA. When the activity of the ETC is maintained, NAD is regenerated and becomes available for repetitive oxidation of glucose. Recently evidence has been found that when $NO_3^-$ is used as an alternative electron acceptor, *E. coli* K12 engages in anaerobic respiration (throughout this disclosure referred to as "AR"), and an increase of up to 50% more ATP is generated for every molecule of glucose that is oxidized. Cell culture of *E. coli* capable of AR reached greater cell density at the end of the growth compared to cells engaged in AF.

This disclosure demonstrates at least two benefits based on a hypothesis that cellular lysate prepared anaerobically via AF would be more productive in CFPS, as these reactions typically encounter limited access to oxygen in static vessels and thus the cells would be conditioned to express above baseline quantities of proteins required for anaerobic fermentation such as lactate or alcohol dehydrogenases. As such, when cell lysate encounters limited oxygen concentrations during CFPS reactions, it is capable of regenerating NAD more efficiently via AF. Second, it was hypothesized that cell lysate prepared from cells preconditioned for AR would be even more efficient than AF conditioned lysate in CFPS reactions that are supplemented with nitrite as the TEA. This is based on a similar assumption that AR conditioned cells will express more metabolic enzymes (complexes such as Nar, Nir and others) that enable them to engage in anaerobic nitrogen metabolism, and therefore produce more ATP compared to AF cells when nitrate is available.

Using cell-free protein expression for any application can be enhanced by increasing the amount of protein that is produced. According to various aspects it is surprisingly and unexpectedly found that conditioning a microorganism under anaerobic conditions prior to lysing the microorganism can improve the initial amount of product (e.g., protein) and final concentration of product that is made by the cell-free protein expression process.

According to various aspects of the present disclosure the microorganism can include a bacteria. The bacteria can be particularly suited to grow under aerobic conditions, anerobic conditions, or both. Examples of suitable bacteria that can be used with the presently described methods include *Streptococcus, Lactobacillus, Bacillus, Escherichia, Salmonella, Neisseria, Acetobacter, Arthrobacter, Aspergillus, Bifdobacterium, Corynebacterium, Pseudomanas*, or a mixture thereof. According to some aspects, a particularly useful microorganism can be *Escherichia coli*.

The microorganism can be a wild-type microorganism or an engineered microorganism. An engineered microorganism may be engineered to overexpress one or more endogenous genes, meaning that the modified cells express the endogenous gene at a higher level than a native cell (e.g., wild-type microorganism) under at least some conditions. In certain of these embodiments, the endogenous gene being overexpressed may be operatively linked to one or more exogenous regulatory elements. For example, one or more exogenous strong promoters may be introduced into a cell such that they are operatively linked to one or more endogenous anaerobic respiration pathway genes.

Anaerobic respiration pathway genes in an engineered microorganism provided herein may be operatively linked to one or more regulatory elements such as a promoter or terminator. As used herein, the term "promoter" refers to an untranslated sequence located upstream (e.g., 5') to the translation start codon of a gene (generally within about 1 to 1000 base pairs (bp), within about 1 to 500 bp) which controls the start of transcription of the gene. The term "terminator" as used herein refers to an untranslated sequence located downstream (e.g., 3') to the translation finish codon of a gene (generally within about 1 to 1000 bp, within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function.

Regulatory elements linked to anaerobic respiration pathway genes in the cells provided herein may be endogenous, exogenous or heterologous. For example, an exogenous anerobic respiration pathway gene may be inserted into a microorganism such that it is under the transcriptional control of an endogenous promoter and/or terminator. Alternatively, the exogenous anaerobic respiration pathway gene may be linked to one or more exogenous regulatory elements. For example, an exogenous gene may be introduced into the cell as part of a gene expression construct that comprises one or more exogenous regulatory elements. In various examples, exogenous regulatory elements, or at least the functional portions of exogenous regulatory elements, may comprise native sequences. In other embodiments, exogenous regulatory elements may comprise non-native sequences. In these embodiments, the exogenous regulatory elements may comprise a sequence with a relatively high degree of sequence identity to a native regulatory element. For example, an exogenous gene may be linked to an exogenous promoter or terminator having at least 50%, at least 60%, at least 70%, at least 80%, or at least 90% sequence identity to a native promoter or terminator. Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. For example, a sequences having an identity score of at least 90%, using the BLAST version 2.2.1 algorithm with default parameters is considered to have at least 90% sequence identity. The BLAST software is available from the NCBI, Bethesda, Md.

Inspection of nucleic acid or amino acid sequences for two nucleic acids or two polypeptides will reveal sequence identity and similarities between the compared sequences. Sequence alignment and generation of sequence identity include global alignments and local alignments which are carried out using computational approaches. An alignment can be performed using BLAST (National Center for Biological Information (NCBI) Basic Local Alignment Search Tool) version 2.2.31 software with default parameters. Amino acid % sequence identity between amino acid sequences can be determined using standard protein BLAST with the following default parameters: Max target sequences: 100; Short queries: Automatically adjust parameters for short input sequences; Expect threshold: 10; Word size: 6; Max matches in a query range: 0; Matrix: BLOSUM62; Gap Costs: (Existence: 11, Extension: 1); Compositional adjustments: Conditional compositional score matrix adjustment; Filter: none selected; Mask: none selected. Nucleic acid % sequence identity between nucleic acid sequences can be determined using standard nucleotide BLAST with the following default parameters: Max target sequences: 100; Short queries: Automatically adjust parameters for short input sequences; Expect threshold: 10; Word size: 28; Max matches in a query range: 0; Match/Mismatch Scores: 1, −2; Gap costs: Linear; Filter: Low complexity regions; Mask: Mask for lookup table only. A sequence having an identity score of XX % (for example, 80%) with regard to a reference sequence using the NCBI BLAST version 2.2.31 algorithm with default parameters is considered to be at least XX % identical or, equivalently, have XX % sequence identity to the reference sequence.

In certain aspects, a regulatory element (e.g., a promoter) linked to an anaerobic respiration pathway gene in the cells provided herein may be foreign to the pathway gene. A regulatory element that is foreign to a pathway gene is a regulatory element that is not linked to the gene in its natural form. A regulatory element foreign to a pathway gene can be native or heterologous, depending on the pathway gene and its relation to the yeast cell. In some instances, a native anaerobic respiration pathway gene is operatively linked to a regulatory element (e.g., a promoter) that is foreign to the pathway gene. In other instances, a heterologous anaerobic respiration pathway gene is operatively linked to an exogenous regulatory element (e.g., a promoter) that is foreign to the pathway gene.

In those embodiments wherein multiple exogenous genes are inserted into a host cell, each exogenous gene may be under the control of a different regulatory element, or two or more exogenous genes may be under the control of the same regulatory elements. For example, where a first exogenous gene is linked to a first regulatory element, a second exogenous gene may also be linked to the first regulatory element, or it may be linked to a second regulatory element. The first and second regulatory elements may be identical or share a high degree of sequence identity, or they be wholly unrelated.

Exogenous genes may be inserted into a microorganism via any method known in the art. In various embodiments, the genes are integrated into the host cell genome. Exogenous genes may be integrated into the genome in a targeted or a random manner. In those embodiments where the gene is integrated in a targeted manner, it may be integrated into the loci for a particular gene, such that integration of the exogenous gene is coupled to deletion or disruption of a native gene. For example, introduction of an exogenous malonic acid, malonate, and esters of malonic acid pathway gene may be coupled to deletion or disruption of one or more genes encoding enzymes involved in other fermentation product pathways. Alternatively, the exogenous gene may be integrated into a portion of the genome that does not correspond to a gene.

Targeted integration and/or deletion may utilize an integration construct. The term "construct" as used herein refers to a DNA sequence that is used to transform a host cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. An integration construct can be assembled using two cloned target DNA sequences from an insertion site target. The two target DNA sequences may be contiguous or non-contiguous in the native host genome. In this context, "non-contiguous" means that the DNA sequences are not immediately adjacent to one another in the native genome, but instead are separated by a region that is to be deleted. "Contiguous" sequences as used herein are directly adjacent to one another in the native genome. Where targeted integration is to be coupled to deletion or disruption of a target gene, the integration construct may also be referred to as a deletion construct. In a deletion construct, one of the target sequences may include a region 5' to the promoter of the target gene, all or a portion of the promoter region, all or a portion of the target gene coding sequence, or some combination thereof. The other target sequence may include a region 3' to the terminator of the target gene, all or a portion of the terminator region, and/or all or a portion of the target gene coding sequence. Where targeted integration is not to be coupled to deletion or disruption of a native gene, the target sequences are selected such that insertion of an intervening sequence will not disrupt native gene expression. An integration or deletion construct is prepared such that the two target sequences are oriented in the same direction in relation to one another as they natively appear in the genome of the host cell. Where an integration or deletion construct is used to introduce an exogenous gene into a host cell, a gene expression cassette is cloned into the construct between the two target gene sequences to allow for expression of the exogenous gene. The gene expression cassette contains the exogenous gene, and may further include one or more regulatory sequences such as promoters or terminators operatively linked to the exogenous gene. Deletion constructs can also be constructed that do not contain a gene expression cassette. Such constructs are designed to delete or disrupt a gene sequence without the insertion of an exogenous gene.

An integration or deletion construct may comprise one or more selection marker cassettes cloned into the construct between the two target gene sequences. The selection marker cassette contains at least one selection marker gene that allows for selection of transformants. A "selection marker gene" is a gene that encodes a protein needed for the survival and/or growth of the transformed cell in a selective culture medium, and therefore can be used to apply selection pressure to the cell. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *K. marxianus* LEU2 gene), uracil (e.g., *K. marxianus, S. cerevisiae,* or *I. orientalis* URA3 gene), or tryptophan (e.g., *K. marxianus, S. cerevisiae,* or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiase) enzyme and confers the ability to grow on melibiose as the sole carbon source). Various selection markers include the URA3 gene, zeocin resistance gene, G418 resistance gene, MEL5 gene, and hygromycin resistance gene. Another selection marker is an L-lactate:ferricytochrome c oxidoreductase (CYB2) gene cassette, provided that the host cell either natively lacks such a gene or that its native CYB2 gene(s) are first deleted or disrupted. A selection marker gene is operatively linked to one or more promoter and/or terminator sequences that are operable in the host cell. In various examples, these promoter and/or terminator sequences are exogenous promoter and/or terminator sequences that are included in the selection marker cassette. Suitable promoters and terminators are as described herein.

An integration or deletion construct is used to transform the host cell. Transformation may be accomplished using, for example, electroporation and/or chemical transformation (e.g., calcium chloride, lithium acetate-based, etc.) methods. Selection or screening based on the presence or absence of the selection marker may be performed to identify successful transformants. In successful transformants, homologous recombination events at the locus of the target site results in the disruption or the deletion of the target site sequence. Where the construct targets a native gene for deletion or disruption, all or a portion of the native target gene, its promoter, and/or its terminator may be deleted during this recombination event. The expression cassette, selection marker cassette, and any other genetic material between the target sequences in the integration construct is inserted into the host genome at the locus corresponding to the target sequences. Analysis by PCR or Southern analysis can be performed to confirm that the desired insertion/deletion has taken place.

In some embodiments, cell transformation may be performed using DNA from two or more constructs, PCR products, or a combination thereof, rather than a single construct or PCR product. In these embodiments, the 3' end of one integration fragment overlaps with the 5' end of another integration fragment. In one example, one construct will contain the first sequence from the locus of the target sequence and a non-functional part of the marker gene cassette, while the other will contain the second sequence from the locus of the target sequence and a second non-functional part of the marker gene cassette. The parts of the marker gene cassette are selected such that they can be combined to form a complete cassette. The cell is transformed with these pieces simultaneously, resulting in the formation of a complete, functional marker or structural gene cassette. Successful transformants can be selected for on the basis of the characteristic imparted by the selection marker. In another example, the selection marker resides on one fragment but the target sequences are on separate fragments, so that the integration fragments have a high probability of integrating at the site of interest. In other embodiments, transformation from three linear DNAs can be used to integrate exogenous genetic material. In these embodiments, one fragment overlaps on the 5' end with a second fragment and on the 3' end with a third fragment.

An integration or deletion construct may be designed such that the selection marker gene and some or all of its regulatory elements can become spontaneously deleted as a result of a subsequent homologous recombination event. A convenient way of accomplishing this is to design the construct such that the selection marker gene and/or regulatory elements are flanked by repeat sequences. Repeat sequences are identical DNA sequences, native or non-native to the host cell, and oriented on the construct in the same or opposite direction with respect to one another. The repeat sequences are advantageously about 50 to 1500 bp in length, and do not have to encode for anything. Inclusion of the repeat sequences permits a homologous recombination event to occur, which results in deletion of the selection marker gene and one of the repeat sequences. Since homologous recombination occurs with relatively low frequency, it may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene. In certain cases, expression of a recombinase enzyme may enhance recombination between the repeated sites.

In various examples of the modified bacteria cells provided herein, the native source gene from which the exogenous malonic acid, malonate, and esters of malonic acid fermentation pathway gene that is derived produces a polypeptide that is involved in a anerobic respiration pathway. In other embodiments, however, the native source gene may encode a polypeptide that is not involved in a anerobic respiration pathway or that catalyzes a reverse reaction in a anerobic respiration pathway. In these embodiments, the exogenous anerobic respiration pathway gene will have undergone one or more targeted or random mutations versus the native source gene that result in modified activity and/or substrate preference. For example, a native source gene may be mutated to generate a gene that encodes a polypeptide with increased activity in a desired reaction direction and/or decreased activity in a non-desired direction in a anerobic respiration pathway. For example, where the native source gene encodes a polypeptide capable of catalyzing both a forward and reverse reactions in a anerobic respiration pathway, the gene may be modified such that the resultant exogenous gene has increased activity in the forward direction and decreased activity in the reverse direction. Similarly, a native source gene may be mutated to produce a gene that encodes a polypeptide with different substrate preference than the native polypeptide. For example, an anerobic respiration pathway gene may be mutated to produce a polypeptide with the ability to act on a substrate that is either not preferred or not acted on at all by the native polypeptide. In these embodiments, the polypeptide encoded by the exogenous malonic acid, malonate, and esters of malonic acid pathway gene may catalyze a reaction that the polypeptide encoded by the native source gene is completely incapable of catalyzing. A native source gene may also be mutated such that the resultant anerobic respiration pathway gene exhibits decreased feedback inhibition at the DNA, RNA, or protein level in the presence of one or more downstream anerobic respiration pathway intermediates or side products.

During conditioning, the microorganism is exposed to substantially anerobic conditions. Substantially anerobic conditions can include an atmosphere that is substantially free of oxygen. For example, the atmosphere can include 0% to 10% oxygen, 3% to 7% oxygen, less than, equal to, or greater than about 0%, 1, 2, 3, 4, 5, 6, 7, 8, 9, or about 10% oxygen. The anerobic environment can be produced by flooding a container with gas that is free of oxygen.

The atmosphere to which the microorganism is exposed can include any gas. As an example, the anaerobic conditions can include about 90 to 99% $N_2$ and about 1 to 10% $CO_2$. The amount of time that the microorganism is exposed to the anerobic environment can be in a range of from about 5 hours to about 48 hours, about 20 hours to about 30 hours, less than, equal to, or greater than about 5 hours, 10, 15, 20, 25, 30, 35, 40, 45, or about 48 hours.

Without intending to be bound to any theory, it is suspected that exposing the microorganism to anerobic conditions can help to prime the microorganism to effectively function later in the cell-free protein expression method when exposed to anerobic conditions. Essentially, when the cell-free protein expression process begins, the microorganism will already be functioning under anerobic conditions and does not have to respond to the anerobic conditions first, before engaging in the cell-free protein expression process.

After the anerobic conditioning is completed. The microorganism is lysed to produce a lysate. Prior to lysing, the microorganism can be centrifuged to concentrate the microorganism in one location. Lysing can include many suitable techniques. As an example, lysing can include suspending the microorganism in a lysing buffer and exposing the microorganism to a lysosome. The lysing buffer can bring the pH of the solution including the microorganism to a range of from about 7 to about 10, about 7 to about 9, less than, equal to, or greater than about 7, 8, 9, or about 10.

Non-limiting examples of proteins of interest that can be formed include superfolder green fluorescent protein, red fluorescent protein, subtilisin BPN', chitinase A, or a mixture thereof. Other proteins of interest can include any protein or combination of proteins that are involved in a metabolic pathway of interest. Additionally, the cell-free protein expression method can be used to produce a protein or mixture of proteins that can in-turn produce a molecule of interest. Some molecules of interest can be a therapeutic. Some proteins of interest can be industrial enzymes. To produce the intended product of the cell-free protein expression method, the lysate can be exposed to at least one of deoxyribonucleic acid (DNA) and ribonucleic acid, and a mixture of phosphoenolpyruvate, amino acids, $NAD^+$, oxalic acid, spermidine, and putrescine. The DNA can be in the form of a DNA template. The DNA template can include a circular vector DNA, a rolling circle amplification DNA product, a linear PCR product, of a mixture thereof.

In some examples, the microorganism can be further conditioned to function under anerobic conditions by supplementing the microorganisms with non-oxygen terminal electron acceptors. For example, the microorganism can be exposed to nitrate, $CO_2$, $SO_4$, Fe(III), Mn(IV), or a combination thereof.

Taken as a whole, it has been found that conditioning the microorganism to anaerobic conditions, supplementing the microorganism with a non-oxygen terminal electron acceptor, or both can increase the initial production of a molecule of interest or protein of interest and increase the production of the same over the course of the cell-free protein expression relative to a comparative microorganism that is exposed to aerobic conditions.

Examples

Various embodiments of the present disclosure can be better understood by reference to the following Examples which are offered by way of illustration. The present disclosure is not limited to the Examples given herein.

Media Preparation and Inoculation. Cells were picked from glycerol stocks and streaked on agarose plates for overnight incubation. Single colonies were picked to prepare seed culture in LB. Seed culture was then washed by centrifugation and resuspension with working media, and used to infect 1 L cultures. All aerobic cultures were prepared in baffled flasks with agitation at 37° C. Rich, 2×YTPG media was standard and included 16 g/L of Tryptone, 10 g/L Yeast Extract, 5 g/L of sodium chloride, and 7 g/L potassium phosphate dibasic, 3 g/L potassium phosphate monobasic autoclaved in a separate container to prevent precipitation. Glucose solution, 18 g/L, was filter sterilized. Evans media used for *E. coli* growth contained Evans base (40 mM K2HPO$_4$, 10 mM NaH$_2$PO$_4$, 10 mM KCl, 1.25 mM MgCl$_2$, 2 mM Na$_2$SO$_4$, 0.38 g/L nitrilotriacetic acid, 0.02 mM CaCl$_2$, pH 7.0, 5 ml/L trace elements solution, and 3 µg/L Na$_2$SeO$_3$·5H$_2$O). This base was supplemented with glucose as carbon source, and nitrogen sources (sodium nitrate or ammonium chloride) which were added separately as needed. The composition of the trace elements is 8 ml/L HCl (37% by volume), 0.412 g/L ZnO, 5.4 g/L FeCl$_3$·6H$_2$O, 2 g/L MnCl$_2$·4H$_2$O, 0.172 g/L CuCl$_2$·2H$_2$O, 0.476 g/L CoCl$_2$·6H$_2$O, 0.064 g/L H$_3$BO$_3$, 0.004 mg/L Na$_2$MoO$_4$·2H$_2$O Cell Growth Conditions. Anaerobic growth experiments were performed in a standard 10 L glass fermenter (New Brunswick). Cells were grown with moderate agitation, and a continuous positive pressure of the 95% N$_2$, 5% CO$_2$ gas, at 37° C. The media was purged with the gas mixture prior to fermentation for 1 hour to remove dissolved oxygen. With both, aerobic and anaerobic growth experiments, samples were pulled to measure OD$_{600}$. The growth was stopped at 2 relative absorbance units (RAU) for rich media cultures, while the minimal media cultures were pulled at 1 RAU.

Lysis. After stopping the growth, cell cultures were drained and kept on ice for the remained of the lysis procedures. Cell culture was centrifuged at 5,000×g for 30 minutes. The resulting cell pellet was washed additional 3 times in the S30 buffer. The buffer included 10 mM Tris, 14 mM Magnesium Acetate, 60 mM Potassium Acetate, 2 mM DTT, and the pH was adjusted to 8.2. In the final step of the wash cycle, cells were resuspended to 1:1 cell paste to buffer solution mixture and transferred to 1.5 ml tubes, 1 ml in each for lysis.

The 1 ml aliquots were then sonicated on the Qsonica Q125 tip sonicator with a 2 mm (5/64") tip for 532 joules with 10 seconds ON/OFF cycles, at 50% amplitude. After sonication, lysed cells were centrifuged at 4 C for 12,000×g for 10 minutes. The supernatant was aliquoted in 250 µl fractions in separate tubes, and flash-frozen with liquid nitrogen.

Master Mix and CFPS reactions. A standard PANOxSP master mix was used. The CFPS reactions were typically 15 µl in total volume, and consisted of 6.3 µl of the master mix, 5 µl of cell lysate, 2 µl of DNA (typically, between 300-500 ng/µl of stock DNA concentration), and 1.7 µl of either supplements or S30 buffer. The reactions were performed on a plate reader (BioTek Synergy Neo 2) with gain set at 60 and excitation/emission parameters set to 488, 509+/−10 nm. Reactions were typically performed for 120 minutes, and at 37° C. unless otherwise detailed in the text.

All sfGFP expressions were made with the pJL1-sfGFP plasmid (Addgene ID: 69496). Comparative analysis of mCherry, Subtilisin BPN, and Chitinase A were made with PCR amplified linear DNA templates with stock concentration of 100 ng/µl.

Comparison to commercial CFPS kits from Promega (S30 T7 High-Yield Protein Expression system) and Arbor Biosciences (myTXTL) was performed according to the manufacturers' manuals. The DNA concentration in kit reactions and in internally prepared reactions was kept the same.

Glove box experiment procedure. Anaerobic CFPS experiments were performed in a glove box. Individual components of CFPS reactions (DNA, lysate, master mix, and buffer) were aliquoted to no more than 50 µl, and degassed in the airlock. Then, the components were mixed in the glove box, and left capped in 1.5 ml tubes to incubate at room temperature for 8 hours. Individual reactions were covered with metal foil to prevent photo degradation of sfGFP. After the reactions were complete, 1.5 ml tubes were removed from the glove box, pipetted up and down to induce better dissolving of oxygen, and incubated at 37° C. in a plate reader where fluorescent maturation of sfGFP took place.

Luminescence. All luminescence experiments were performed with Promega's CellTiter Glo2.0. CFPS reactions were diluted with S30 buffer either 10, 100 or 1000× prior to application of the kit.

Aerobically and Anaerobically Cultured *E. coli*-based CFPS Lysates. To test the effect of anaerobic cell culture on the performance of CFPS reactions, *E. coli* BL21DE3 Star cells was prepared in both rich (2×YTPG) and defined (Evans) media. Evans media was supplemented with a reduced carbon (glucose) and nitrogen (sodium nitrate, ammonium chloride or both) sources. Rich media cultures were propagated only aerobically (atmospheric oxygen concentration), while defined media cell cultures were prepared both aerobically and anaerobically (95% N$_2$, 5% CO$_2$ or atmospheric oxygen concentration in air). Defined media was used to control what metabolic pathway *E. coli* cells could use during anaerobic growth. The type of nitrogen source present in the defined media serves a dual function. First, ammonium contributes solely to anabolism (building block of amino acids and other molecules), thereby constraining cells to engage entirely in AF (due to the lack of any TEAs). Second, in the AR pathway, nitrate begins by serving as an electron acceptor, in the absence of oxygen, and gets converted to nitrite by the NarR enzyme. Then, the product, nitrite, gets converted to ammonium by the NirB enzyme, and is either used for anabolism or gets excreted. The conversion of nitrite to ammonium takes place concurrently with oxidation of NADH, which regenerates NAD to make it available for anaerobic oxidation of glucose.

Cell cultures were then prepared and lysed via a standard tip sonication protocol described previously and in the methods section of these examples. The capacity of the cell lysates to synthesize a common reporter protein, sfGFP, was used to test overall productivity. Both, the initial rate of change of the fluorescent signal and total fluorescent signal produced in a CFPS reaction were the metrics to quantify productivity. A linear transfer function can be used to convert these relative fluorescent units to mg/mL concentrations, if desired, but for the focus of this work in comparing lysate performance, relative fluorescence is a suitable measure since all experimental conditions are held constant (plate reader settings and CFPS reaction conditions).

Figure 1A:
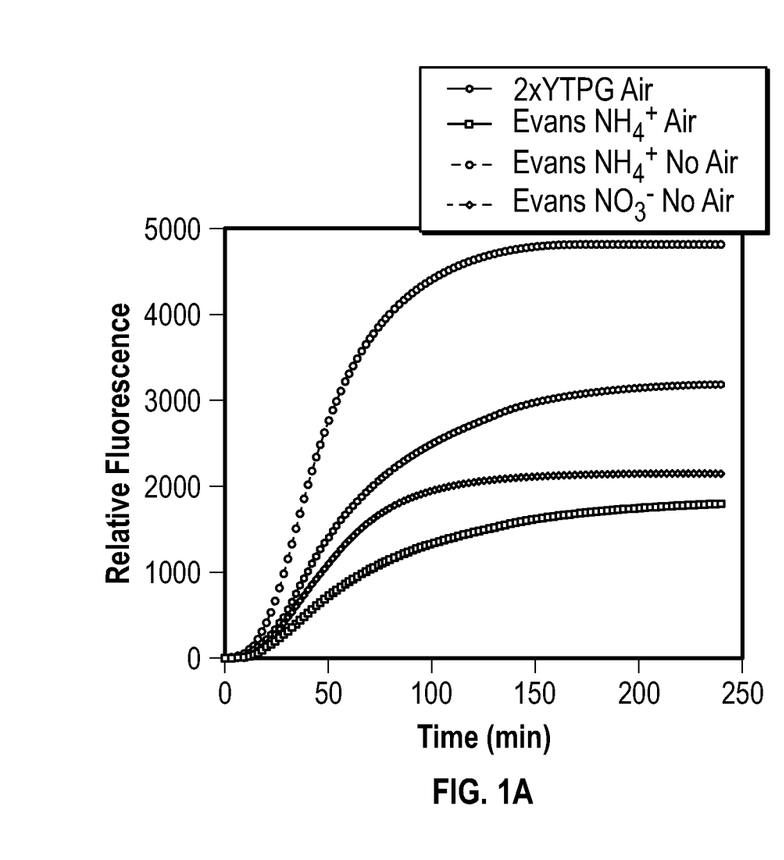
FIG. 1A is a time resolved fluorescence signal graph from sfGFP produced from CFPS reactions containing various lysates: "2×YTPG" is a standard rich media, cultured here only in aerobic conditions in shaker flasks ("air") as a benchmark for current CFPS methods; "Evans" is a glucose-containing, defined, minimal media supplemented with different sources of nitrogen. Supplementation with ammonium ($NH_4^+$) forces lysate to use oxygen as a terminal electron acceptor during aerobic culture in shaker flasks ("air") or perform fermentation (when atmospheric oxygen is replaced with a mixture of 95% $N_2$ and 5% in a bio fermenter $CO_2$—"no air"). Supplementation with nitrate ($NO_3^-$) forces cells to engage in Anaerobic Respiration (cells were cultured in a bio fermenter under "no air" conditions).

When comparing the performance of aerobically prepared lysates (cells cultured in rich media or minimal media supplemented with ammonium), it is evident that both (1) initial protein synthesis rate, and (2) total reporter protein synthesis was greater for rich media lysate (FIG. 1A—"2× YTPG" and "Evans $NH_4^+$ air" respectively). Initial rate was defined as the slope of the linear model plotted at the log phase of protein expression (fixed time window of 20 to 50 minutes after incubation start. The difference in performance of cells grown on minimal media and rich media can be attributed to a variety of factors such as acid stress, or focus on anabolism instead of replication to name a few—but is still a poorly understood phenomena.

A better comparison is to use lysates that were both prepared on identical minimal media (Evans supplemented with ammonium), but cultured either aerobically or anaerobically. As a reminder, in this case, anaerobically prepared lysate engages solely in AF, while the aerobically prepared lysate oxidizes glucose with oxygen as a TEA, similar to cells grown aerobically on 2×YTPG media. The anaerobic lysate produces almost 2.6 times more fluorescence signal, with 4.0 times higher initial protein synthesis rate, compared to the aerobic lysate (FIG. 1A—Evans $NH_4^+$ air and no air). Moreover, the anaerobically prepared extract produced 1.5 times more sfGFP than the standard method (rich media, cultured aerobically). This indicates that anaerobic preparation of the CFPS cell lysate can provide a significant advantage in productivity of CFPS reactions.

However, to provide a more mechanistic insight, AR cell lysate (prepared anaerobically with minimal media supplemented with nitrate) was compared to lysate prepared aerobically on minimal media that is supplemented with ammonium (capable of aerobic oxidation of glucose). The AR lysate performed only marginally better than the aerobic lysate (FIG. 1A—Evans $NO_3^-$ no air and 2×YTPG). This was likely due to increased stress on cells grown in minimal media compared to rich media.

Benchmarking Anaerobic Lysates against Standard Lysates. To further compare performance of anaerobically conditioned lysate, a yield (at 2 h incubation, 37° C.) was benchmarked against a common literature lysate (cells grown aerobically on rich 2×YTPG media) as well as two commercial kits (Promega's S30 T7 High-yield protein expression system and Arbor Biosciences' myTXTL). Based on a custom fluorescent calibration curve, the anaerobically conditioned cells produced approximately 600 μg/mL sfGFP, which was 2.2, 1.7, and 2.0 times the yields of 2×YTPG, Promega and myTXTL respectively. This panel was run again for a longer expression period, which again confirmed a fast peak yield of the anaerobically conditioned lysate (<2 h) with myTXTL eventually reaching the same expression level at 12 h.

Figure 3A:
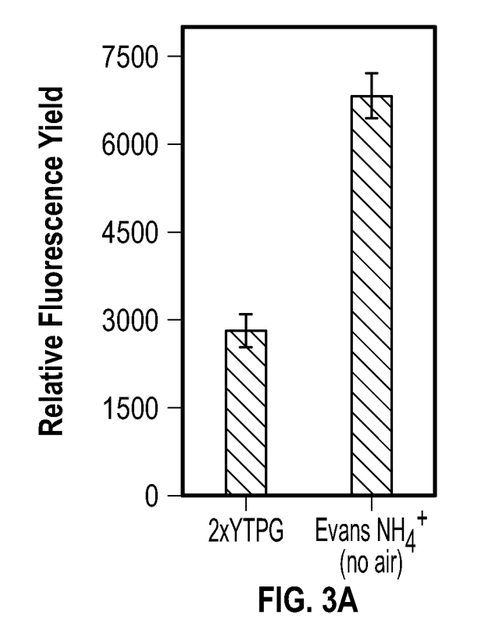
FIG. 3A comparison of reporter protein expression yield in CFPS reactions composed with the standard 2×YTPG and Anaerobic Fermentation capable lysate (Evans $NH_4^+$ no air). (A) Expression yield of sfGFP (from pJL1 plasmid DNA template) after incubation at 37° C. for 2 hours, measured in relative fluorescence units.
Figure 3B:
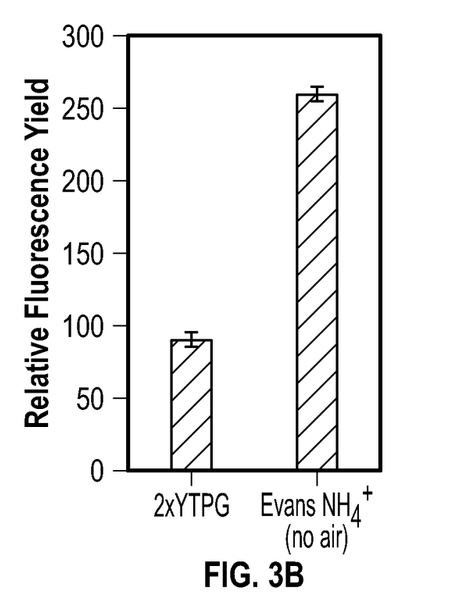
FIG. 3B is a graph showing an expression yield of mCherry (from PCR amplified linear DNA template), measured in relative fluorescence units.
Figure 3C:
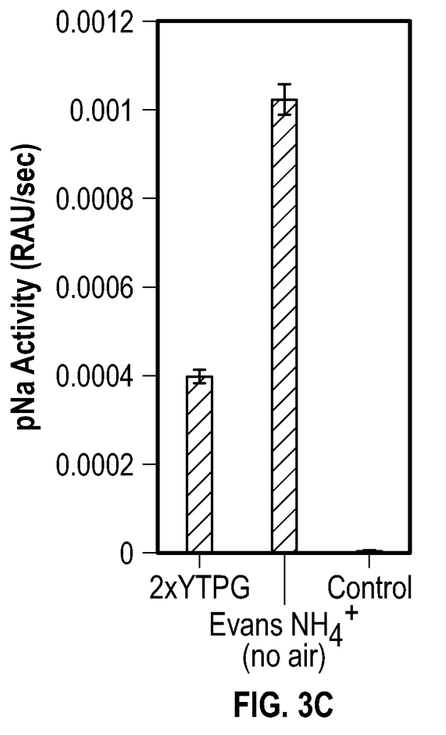
FIG. 3C is a graph showing expression yield of Subtilisin BPN (from PCR amplified linear DNA template), reported as protein activity. CFPS reaction without DNA is used as a "Control".
Figure 3D:
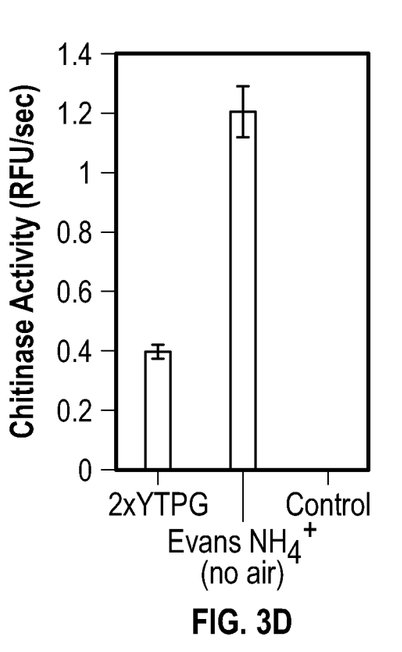
FIG. 3D is a graph showing expression yield of Chitinase A (from PCR amplified linear DNA template), reported as protein activity. CFPS reaction without DNA is used as a "Control". All error bars represent 1 standard deviation (n=3).

Relative Expression of Other Reporter Proteins. In order to determine that anaerobic conditioning provides a global advantage and not constrained to a specific protein or its maturation, three additional reporter proteins (mCherry, Subtilisin BPN (apr) and Chitinase A (prchia A)) were expressed with standard 2×YTPG and AF capable lysates. Originally, it was demonstrated that the AF capable lysate produces roughly 144% more sfGFP than the standard 2×YTPG lysate (FIG. 3A). When testing the productivity of the AF capable against the 2×YTPG lysate it was demonstrated that the former is 188%, 158% and 206% percent more productive at expressing mCherry, Subtilisin BPN and Chitinase A respectively (FIGS. 3B, C and D). This observation indicates that the AF capable lysate improves expression in a broad class of proteins. These reporter proteins lack disulfide bonds, and have been shown to work well in prior cell-free work. Proteins with disulfide bonds can be expressed using anaerobically prepared cell-free lysate, but higher yields will likely be achieved if a strain optimized for disulfide bond formation is used.

Figure 1B:
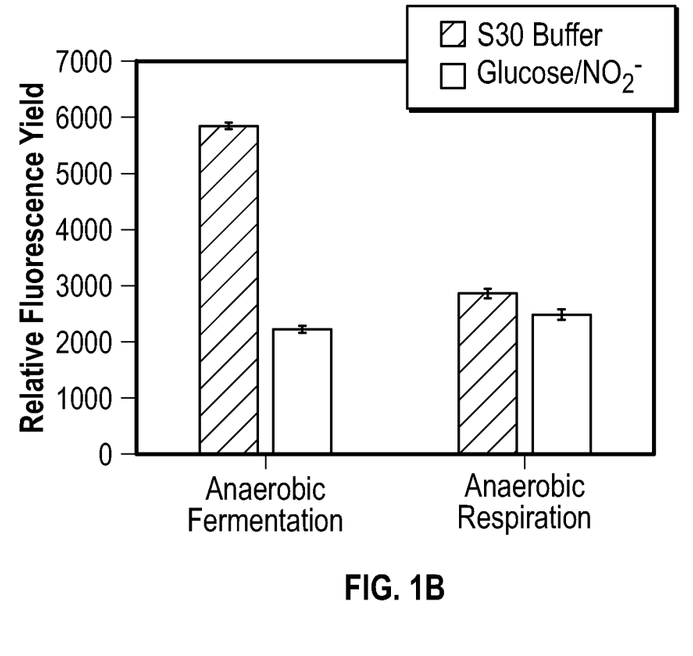
FIG. 1B is a fluorescence graph (background subtracted) of sfGFP from CFPS reactions composed of *E. coli* lysate that was conditioned to engage in either anaerobic fermentation (AF) or anaerobic respiration (AR) and were supplemented with 40 mM glucose and 40 mM $NO_2^-$ ("Glucose/$NO_2^-$") or S30 reaction buffer ("S30 buffer"). All error bars represent 2 standard deviations (n=2).

Nitrite Supplementation and Optimization in CFPS Reactions. Additionally, it was evaluated whether the supplementation of nitrite as an alternate TEA to CFPS reactions would improve sfGFP synthesis. To achieve this, the cell lysate was prepared to have AR capacity (expressed NirB and other proteins of the Nar pathway), and the AF lysate, since the former was expected to generate 50% more ATP during glucose oxidation (FIG. 1D). However, it was observed that the addition of nitrite (at 40 mM) to the CFPS reaction decreases sfGFP expression in each case (FIG. 1B). Yet it is important to note that the CFPS reactions with AR lysate have less of a change in sfGFP expression due to nitrite addition compared to AF lysate (relative loss in efficiency was 13% for the AR lysate and 38% for the AF lysate—FIG. 1B). This could indicate that the AR lysate is more efficient at oxidizing glucose than the AF lysate when nitrite is present but that this concentration of nitrate may not be optimal.

Although the supplementation experiments indicated a positive effect of nitrite on cells harboring NirB vs. cells lacking this overexpression, the addition of nitrite at 40 mM decreased the performance of CFPS reactions in all trials. This could be due to toxicity of nitrite or the imbalance of the ionic strength of the CFPS reaction caused by the increase in counter ions (sodium and other impurities) at high concentrations of nitrite. It was also attempted to identify a nitrite supplement concentration that increases the efficiency of glucose oxidation, while minimizing the toxicity effect to the CFPS reaction.

Figure 4:
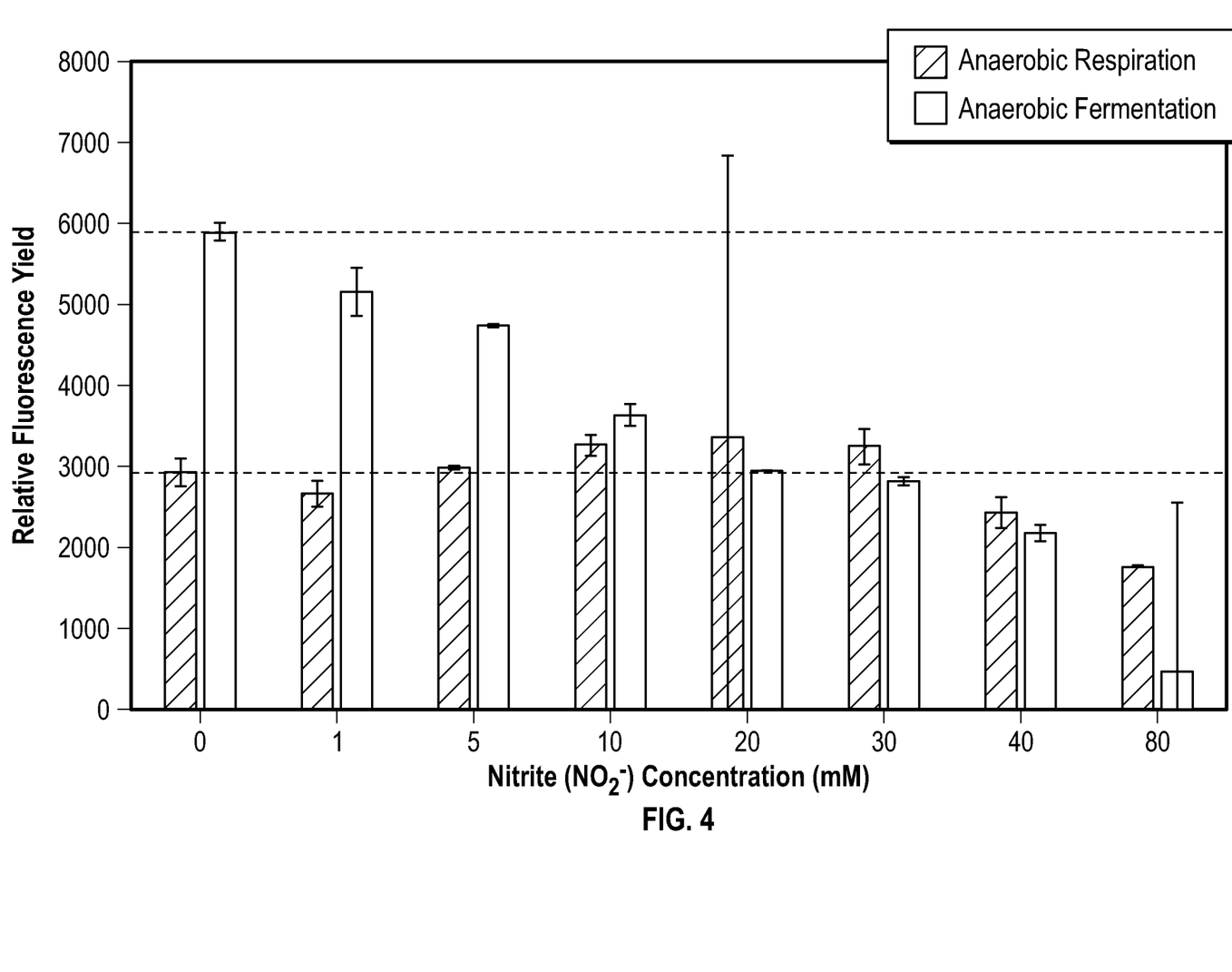
FIG. 4 is a graph showing end fluorescence (background subtracted) of sfGFP produced from CFPS reactions composed with Anaerobic Fermentation and Anaerobic Respiration conditioned *E. coli* lysate that were supplemented with 40 mM glucose and various (0-80 mM) concentrations of $NO_2^-$. Grey and Red dotted lines are Anaerobic Fermentation and Anaerobic Respiration baselines (RFU yield at Nitrite concentration 0 mM). All error bars represent 2 standard deviations (n=2).

CFPS reactions were tested with various concentrations of nitrite (0 to 80 mM) using the AF and AR lysates. In both cases the effect of nitrate is measured by referencing to the 0 mM level of individual lysates. In this panel, it was observed that the ideal concentration of nitrite ranges from 10-30 mM for AR lysate. In fact, any nitrate supplement above 1 mM and below 40 mM provides a gain in performance of CFPS reactions in AR lysate relative to no nitrate (FIG. 4). While there were outliers in this nitrite gradient experiment (at 20 and 80 mM nitrite), it was repeated 3 times, and consistent results were observed. Even though the overall performance (capacity to express protein of interest—sfGFP) of AR lysate is less than AF in this experiment, this supplementation effect would have great utility when oxygen concentrations are limited.

In control experiments, this test was repeated with the lysate supplemented with both ammonium and nitrate during growth. The CFPS reactions with this lysate did not exhibit a pronounced gain in performance when supplemented with nitrite in the master mix, unlike the lysate prepared only with nitrate during growth. It was speculated that this was due to lower levels of NirB available in the lysate to turnover nitrite (less available from conditioning).

Figure 5:
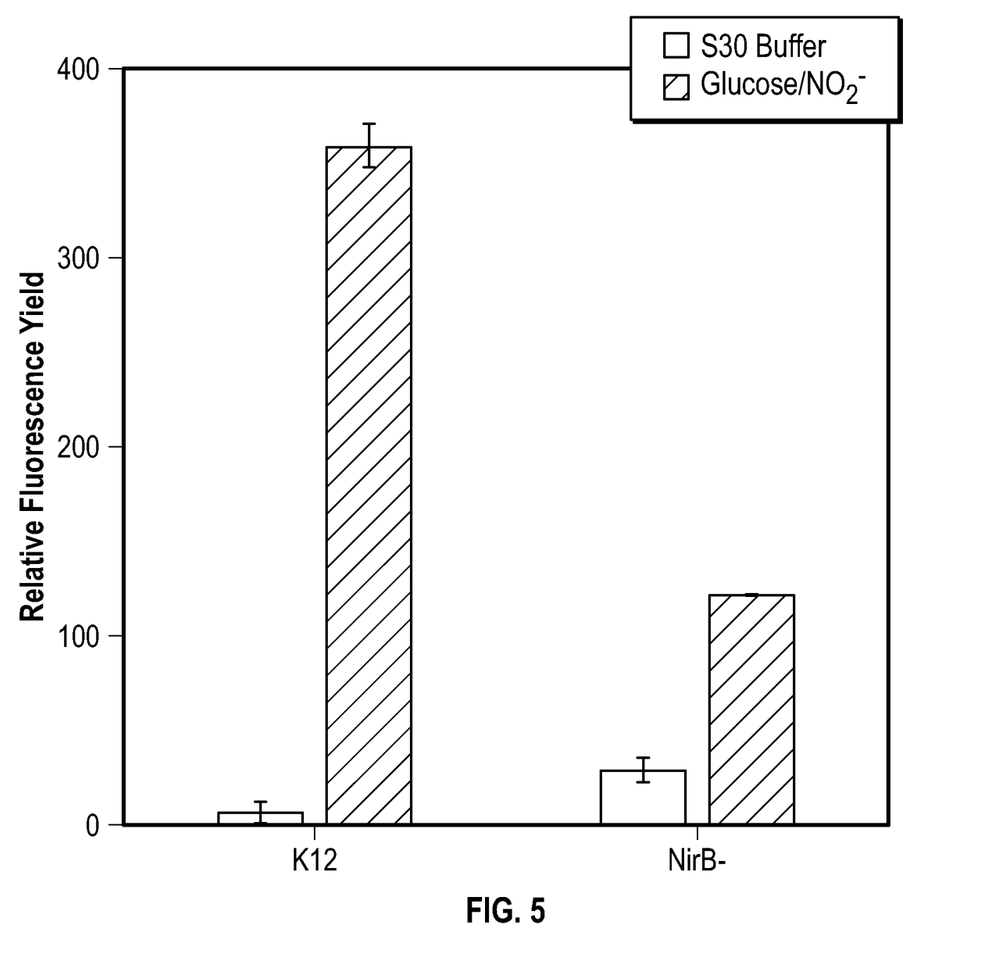
FIG. 5 is a graph showing end fluorescence (background subtracted) of sfGFP produced by CFPS reactions using AR-conditioned *E. coli* K12 and *E. coli* K12 NirB knockout (NirB−) lysates that were supplemented with 40 mM Glucose and either 20 mM $NO_2^-$ ("Glucose/$NO_2^-$") or S30 buffer ("S30 Buffer"). All error bars represent 3 standard deviations (n=2).

Anaerobic Respiration Capacity of the *E. coli* K12 NirB Knockout. These examples show that (1) anaerobic preparation of cell lysate (AF) significantly improves the productivity of CFPS reactions, (2) Anaerobic Respiration (AR) allows for more efficient oxidation of glucose, and (3) an optimal nitrite supplement concentration exists for AR prepared cells to minimize toxicity to cell-free reactions while serving as an alternate TEA. However, further insight on the mechanistic reason that the reduction of NADH by NirB facilitates efficient oxidation of glucose rather than some orthogonal pathway may be beneficial. To test this hypothesis, additional CFPS reactions were prepared with *E. coli* K12 and K12 NirB knockout lysates conditioned to engage in AR (FIG. 5). These CFPS reactions contained 40 mM glucose and were either supplemented with the optimal concentration of nitrite (20 mM) or S30 buffer.

Without nitrite, CFPS reactions with the wild type lysate yielded similar, low-level fluorescence as the knockout. However, when supplemented with nitrite, the wild type lysate performs three times better than the knockout lysate, a statistically significant gain in performance (FIG. 5). Notably, there is still a considerable increase in performance when NirB knockout lysate is supplemented with nitrite. This was likely due to the overcompensation of the damaged Nar pathway with the activity of the Nap pathway present in anaerobic nitrogen respiration. These experiments reinforce the hypothesis that cells which are conditioned to engage in AR oxidize glucose more efficiently, by relying less on alcohol or lactate dehydrogenases, producing more acetate, and regenerating NAD via soluble NirB. In addition, this demonstrated that NirB's capacity to oxidize NADH plays a crucial role in facilitating this increase in efficiency. However, there are other anaerobic respiration pathways that can be explored in an effort to optimize the performance of CFPS reactions.

For this experiment, it is important to note that *E. coli* CFPS reactions are commonly performed with strains engineered for increased heterologous protein expression (elimination of proteases and stabilization of genetic templates, such as the common BL21 DE3 Star) rather than K12, which readily explains the decreased level of expression observed in these experiments (RFU levels compared between FIGS. 5 and 1).

CFPS Performance when Oxygen is Limited. Even with an optimal concentration of nitrite supplemented to CFPS reactions with AR conditioned lysate, it was observed that only a 32% increase in performance (FIG. 4). Upon further reflection, it was realized that these CFPS reactions had access to dissolved oxygen, and thus likely engaged in some aerobic respiration concurrently. It is possible that the overall gain in performance of AR-conditioned CFPS reactions is masked by the accessibility to dissolved oxygen. Indeed the importance of oxygen is found in other CFPS publications that encourage large surface area, small volume experiments. To more carefully test this theory, CFPS reactions were conducted in controlled, anaerobic conditions using a glove box filled with 95% argon and 5% hydrogen gas mixture instead of atmospheric air.

Figure 6A:
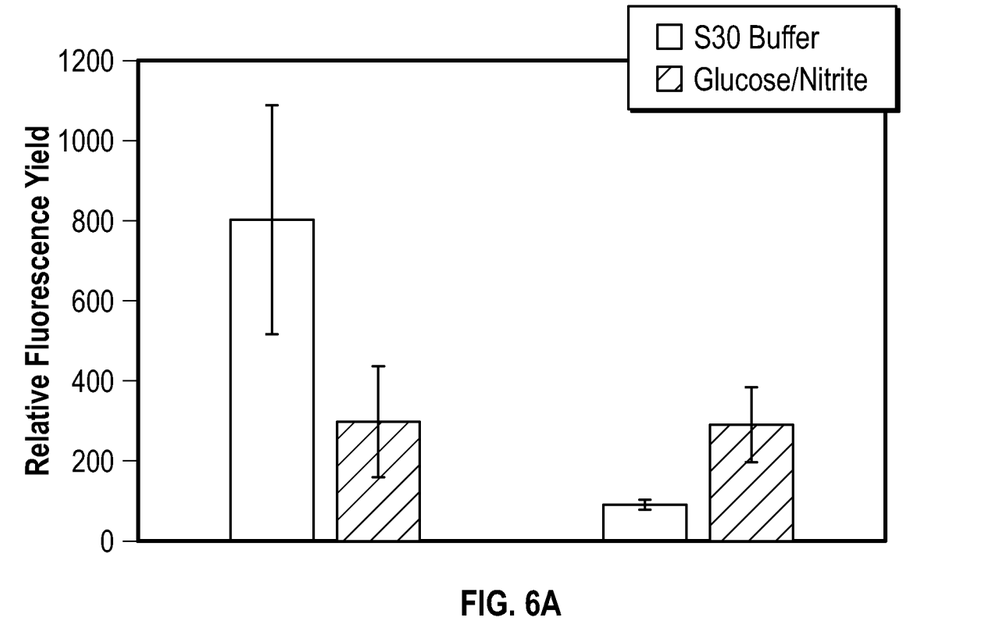
FIG. 6A is a graph showing end fluorescence (background subtracted) of sfGFP produced in CFPS reactions using AF and AR conditioned lysate that were performed under anaerobic conditions (glove box with 95% Ar, 5% $H_2$). The reactions were supplemented with 40 mM Glucose and either 20 mM $NO_2^-$ ("Glucose/$NO_2^-$") or S30 buffer ("S30 Buffer").
Figure 6B:
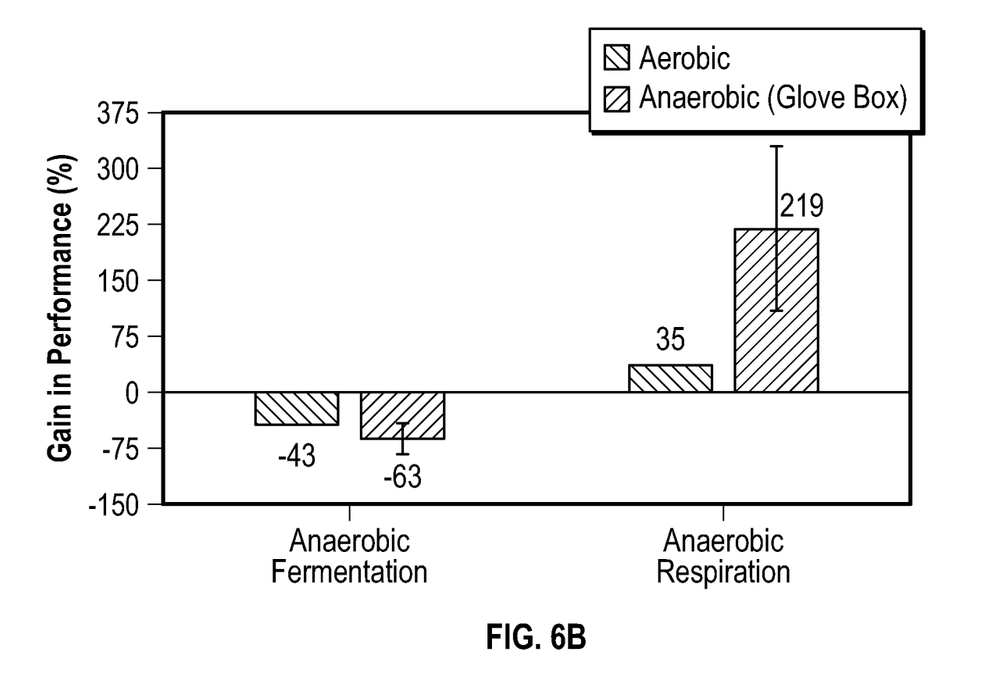
FIG. 6B is a graph comparing gain (or loss) in performance (%) compared to S30 control when supplemented by 40 mM Glucose, and 20 mM $NO_2^-$. Aerobic reaction reactions were performed under atmospheric oxygen concentrations, while anaerobic reactions were performed in the glove box (95% Ar, 5% $H_2$). Error bars represent 1 standard deviation n=2 samples.

CFPS reactions conducted in the glove box were composed of AF and AR conditioned lysates. These reactions were supplemented with glucose and an optimal concentration of nitrite (20 mM) or S30 buffer to fill the void volume. The AF lysate yielded less fluorescence than the S30 buffer control when supplemented with nitrite, whereas the AR lysate demonstrated a marked improvement (FIG. 6). This reinforces the theory that CFPS reactions perform worse when no oxygen is available as a TEA to facilitate aerobic respiration; furthermore, it indicates that AR provides a significant advantage in productivity when oxygen is limited by supplying an alternative TEA.

In sum, the examples investigated preconditioning of cells to AF and AR metabolism prior to forming lysate as well as supplementing an alternative TEA to increase the efficiency of glucose oxidation and thereby the productivity of CFPS reactions. The results obtained using sfGFP as a reporter protein are encouraging. AF lysate increases the rate of initial protein expression by 4× and increases the end yield by 50% (FIG. 1A) when compared to standard lysate that is cultured aerobically in rich media; these improvements are seen when the CFPS reactions are run in typical aerobic conditions (e.g. on a counter top, minimal mixing, small reactor volumes). However, an even greater impact of pre-conditioned lysate and alternative TEA becomes apparent when CFPS reactions are run in oxygen limited conditions; when the AR-lysate supplemented with nitrite is used to produce sfGFP in an anaerobic glovebox, it was observed that a 2× increase in yield over reactions that were not supplemented with TEA.

Figure 2:
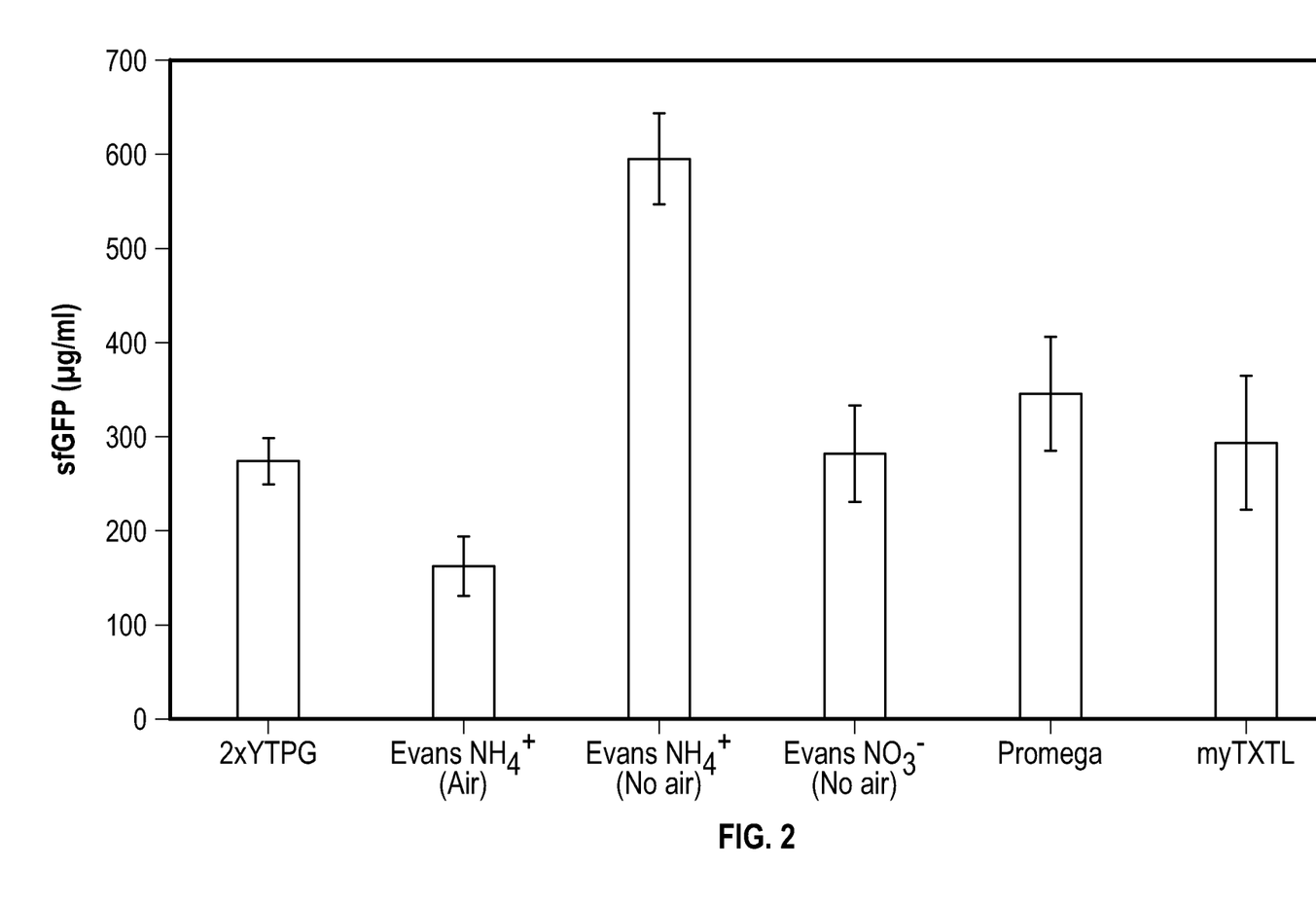
FIG. 2 shows sfGFP yield in CFPS reactions after incubation for 2 hours at 37° C. reported in (mg/ml). A standard 2×YTPG lysate was compared to minimal media aerobic (Evans $NH_4^+$ Air), AF capable (Evans $NH_4^+$ No air), AR capable (Evans $NO_3^-$ No air) lysates. None of the conditions were supplemented with glucose or nitrite. All of these lysates were also compared to kit reactions (same DNA concentration across all reaction conditions) from Promega (S30 T7 High-Yield Protein Expression System), and Arbor Biosciences (myTXTL) each using their respective supplement mixes (a custom master mix used with 2×YTPG and anaerobic lysates). All error bars represent 1 standard deviation (n=3).

In all the baseline experiments (master mix not supplemented with nitrite or glucose) that the AF lysate outperformed AR lysate (FIGS. 1B and 2). Thus, if maximizing protein expression yield and rate in a typical CFPS reaction (well plate run in atmosphere) is the goal, the AF lysate may be the best choice in this current panel. However, the findings on AR lysate supplementation by nitrate augers even greater potential of the AR lysate. During cell growth, the AF (FIG. 1A—Evans $NH_4^+$ no air) and the AR (FIG. 1A—Evans $NO_3^-$ no air) lysates were both prepared anaerobically but they use different growth media (AF is prepared on ammonium as a nitrogen source while AR contained only nitrate). In the case of AR, the *E. coli* cells must convert nitrate to ammonium for anabolic (protein building) purposes via Nar and Nir protein complexes; this appears to stress the cells as they took longer to begin growth during fermentation (data not shown) leading to a less efficient extract. This is attributed to the fact that during the growth, a sufficient concentration of ammonium needs to be generated via dissimilatory nitrate reduction for normal metabolic processes of the cell to begin.

This study uncovers a few other topics for further improvement of anaerobic conditioned cell lysate. While one anaerobic metabolism pathway was explored, the Nar pathway of anaerobic nitrogen metabolism, it is important to note that bacteria can use many alternative TEAs. The major purpose of this adaptive feature is to oxidize glucose more efficiently, generating ATP via oxidative phosphorylation, even in the absence of oxygen. It is possible that other anaerobic metabolism pathways could increase the efficiency of CFPS by an even greater amount. Moreover, the cell line could undergo further synthetic design to greater utilize these pathways (much like the work on protease knockouts to boost productivity). For example, it would be possible to overexpress Nir protein in the cells prior to lysis, which is readily soluble and is responsible for regeneration of $NAD^+$, to achieve even greater productivity.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Additional Embodiments

The following exemplary embodiments are provided, the numbering of which is not to be construed as designating levels of importance:

Aspect 1 provides a cell-free protein expression method comprising:
exposing a microorganism to substantially anaerobic growth conditions to produce a conditioned microorganism;
lysing the conditioned microorganism to produce a lysate;
combining the lysate with a nucleic acid and producing a protein of interest a metabolic pathway, a molecule, or a mixture thereof from the lysate.

Aspect 2 provides the method of Aspect 1, wherein the microorganism comprises a bacteria.

Aspect 3 provides the method of any one of Aspects 1 or 2, wherein the microorganism comprises a bacteria adapted to grow under aerobic conditions, anerobic conditions, or both.

Aspect 4 provides the method of any one of Aspects 1-3, wherein the microorganism comprises a bacteria capable of growing under anerobic conditions.

Aspect 5 provides the method of any one of Aspects 1-4, wherein the microorganism comprises *Streptococcus, Lactobacillus, Bacillus, Escherichia, Salmonella, Neisseria, Acetobactor, Arthrobacter, Aspergillus, Bifdobacterium, Corynebacterium, Pseudomanas*, or a mixture thereof.

Aspect 6 provides the method of any one of Aspects 1-5, wherein the microorganism comprises *Escherichia coli.*

Aspect 7 provides the method of any one of Aspects 1-6, wherein the microorganism comprises an engineered microorganism.

Aspect 8 provides the method of any one of Aspects 1-7, wherein exposing the microorganism to substantially anerobic conditions comprises exposing the microorganism to an atmosphere that is free of oxygen.

Aspect 9 provides the method of any one of Aspects 1-8, wherein exposing the microorganism to substantially anaerobic conditions comprises exposing the microorganism to an atmosphere comprising about 90 to 99% N2 and about 1 to 10% CO2.

Aspect 10 provides the method of any one of Aspects 1-9, wherein the microorganism is exposed to substantially anaerobic conditions for a time in a range of from about 5 hours to about 48 hours.

Aspect 11 provides the method of any one of Aspects 1-10, wherein the microorganism is exposed to substantially anaerobic conditions for a time in a range of from about 20 hours to about 30 hours.

Aspect 12 provides the method of any one of Aspects 1-11, wherein the conditioned microorganism is centrifuged to form a cell pellet prior to lysing.

Aspect 13 provides the method of Aspect 12, further comprising washing the cell pellet with a buffer.

Aspect 14 provides the method of any one of Aspects 1-13, wherein a pH of the lysate is in a range of from about 7 to about 10.

Aspect 15 provides the method of any one of Aspects 1-14, wherein a pH of the lysate is in a range of from about 7 to about 9.

Aspect 16 provides the method of any one of Aspects 1-15, wherein producing the protein of interest comprises exposing the lysate to at least one of deoxyribonucleic acid and ribonucleic acid, and a mixture of phosphoenolpyruvate, amino acids, NAD+, oxalic acid, spermidine, and putrescine.

Aspect 17 provides the method of any one of Aspects 1-16, wherein producing the protein of interest further comprises exposing the lysate to a DNA template.

Aspect 18 provides the method of Aspect 17, wherein the DNA template comprises a circular vector DNA, a rolling circle amplification DNA product, a linear PCR product, of a mixture thereof.

Aspect 19 provides the method of any one of Aspects 1-18, wherein the microorganism prior to lysing produces more proteins associated with anaerobic respiration than a comparative microorganism grown under aerobic conditions.

Aspect 20 provides the method of any one of Aspects 1-19, wherein the protein of interest comprises superfolder green fluorescent protein, red fluorescent protein, subtilisin BPN', chitinase A, or a mixture thereof.

Aspect 21 provides the method of any one of Aspects 1-20, wherein the method produces a greater quantity of the protein of interest than a comparative method using an aerobically conditioned microorganism.

Aspect 22 provides the method of any one of Aspects 1-21, wherein exposing a microorganism to substantially anaerobic conditions further comprises supplementing the microorganism with nitrate, CO2, SO4, Fe(III), Mn(IV), or a combination thereof.

Aspect 23 provides the method of any one of Aspects 7-22, wherein the engineered microorganism overexpresses or presents one or more enzymes associated with an anerobic respiration pathway compared to a corresponding wild type microorganism.

What is claimed is:

1. A cell-free protein expression method comprising:
exposing a microorganism to substantially anaerobic growth conditions to produce a conditioned microorganism;
lysing the conditioned microorganism to produce a lysate; and
combining the lysate with a nucleic acid and producing a protein of interest, a combination of proteins of interest, a molecule, or a mixture thereof from the lysate,
wherein exposing the microorganism to substantially anaerobic conditions comprises exposing the microorganism to an atmosphere comprising about 90 to 99% $N_2$ and about 1 to 10% $CO_2$ for a time in a range of from about 5 hours to about 48 hours and the microorganism is bacteria selected from comprises-*Streptococcus* bacteria, *Lactobacillus* bacteria, *Bacillus* bacteria, *Escherichia* bacteria, *Salmonella* bacteria, *Neisseria* bacteria, *Acetobactor* bacteria, *Arthrobacter* bacteria, *Aspergillus* bacteria, *Bifdobacterium* bacteria, *Corynebacterium* bacteria, *Pseudomanas* bacteria, or a mixture thereof.

2. The method of claim 1, wherein the microorganism comprises *Escherichia coli*.

3. The method of claim 1, wherein the microorganism comprises an engineered microorganism.

4. The method of claim 1, wherein exposing the microorganism to substantially anerobic conditions comprises exposing the microorganism to an atmosphere that is free of oxygen.

5. The method of claim 1, wherein the microorganism is exposed to substantially anaerobic conditions for a time in a range of from about 20 hours to about 30 hours.

6. The method of claim 1, wherein the conditioned microorganism is centrifuged to form a cell pellet prior to lysing.

7. The method of claim 6, further comprising washing the cell pellet with a buffer.

8. The method of claim 1, wherein a pH of the lysate is in a range of from about 7 to about 10.

9. The method of claim 1, wherein a pH of the lysate is in a range of from about 7 to about 9.

10. The method of claim 1, wherein producing the protein of interest comprises exposing the lysate to at least one of deoxyribonucleic acid and ribonucleic acid, and a mixture of phosphoenolpyruvate, amino acids, NAD$^+$, oxalic acid, spermidine, and putrescine.

11. The method of claim 1, wherein producing the protein of interest further comprises exposing the lysate to a DNA template.

12. The method of claim 11, wherein the DNA template comprises a circular vector DNA, a rolling circle amplification DNA product, a linear PCR product, of a mixture thereof.

13. The method of claim 1, wherein the microorganism prior to lysing produces more proteins associated with anaerobic respiration than a comparative microorganism grown under aerobic conditions.

14. The method of claim 1, wherein the protein of interest comprises superfolder green fluorescent protein, red fluorescent protein, subtilisin BPN', chitinase A, or a mixture thereof.

* * * * *